(12) United States Patent
Levy et al.

(10) Patent No.: US 10,149,935 B2
(45) Date of Patent: Dec. 11, 2018

(54) DELIVERY SYSTEM AND METHOD FOR THE EFFECTIVE AND RELIABLE DELIVERY OF CONTROLLED AMOUNTS OF A MEDICAL FLUID

(71) Applicants: Frank Levy, Fort Myers, FL (US); Kimberley Levy, Fort Myers, FL (US)

(72) Inventors: Frank Levy, Fort Myers, FL (US); Kimberley Levy, Fort Myers, FL (US)

( * ) Notice: Subject to any disclaimer, the term of this patent is extended or adjusted under 35 U.S.C. 154(b) by 301 days.

(21) Appl. No.: 15/091,055

(22) Filed: Apr. 5, 2016

(65) Prior Publication Data

US 2016/0213835 A1    Jul. 28, 2016

Related U.S. Application Data

(63) Continuation-in-part of application No. 14/497,657, filed on Sep. 26, 2014, now Pat. No. 9,427,522, which
(Continued)

(51) Int. Cl.
*A61M 5/00* (2006.01)
*A61M 39/22* (2006.01)
(Continued)

(52) U.S. Cl.
CPC ............... *A61M 5/007* (2013.01); *A61B 5/00* (2013.01); *A61J 1/2037* (2015.05); *A61J 1/2062* (2015.05);
(Continued)

(58) Field of Classification Search
CPC ............... A61M 5/007; A61M 5/1407; A61M 5/16827; A61M 5/178; A61M 5/36; A61M 5/158
See application file for complete search history.

(56) References Cited

U.S. PATENT DOCUMENTS 3,004,686 A    10/1961  McKee
3,831,844 A    8/1974   Tropeano et al.
(Continued)

FOREIGN PATENT DOCUMENTS

CN    2179152 Y    10/1994
DE    10161027 A1    6/2003
(Continued)

*Primary Examiner* — Edelmira Bosques
(74) *Attorney, Agent, or Firm* — Welsh Flaxman & Gitler LLC

(57) ABSTRACT

A method for performing a medical procedure requiring effective, reliable and foolproof delivery of controlled amounts of a medical grade gas to a patient includes providing a compressed gas cylinder having a weight with medical grade gas sealed therein of at least twelve grams and not greater than fifty grams. The method also includes connecting the compressed gas cylinder to an integrated compressed gas unit including a regulator valve assembly positioned between an outlet port and an inlet port, wherein the regulator valve assembly includes a press button actuator and regulator adjustment dial. A flow control system is secured to the compressed gas unit and the medical grade gas is delivered in precisely controlled amounts by actuating the compressed gas unit and operating the flow control system to deliver the medical grade gas to vasculature of the patient.

9 Claims, 11 Drawing Sheets

Related U.S. Application Data is a continuation-in-part of application No. 13/857,448, filed on Apr. 5, 2013, now Pat. No. 9,486,594, which is a continuation-in-part of application No. 13/068,680, filed on May 17, 2011, now Pat. No. 8,876,749, which is a continuation-in-part of application No. 12/652,845, filed on Jan. 6, 2010, now abandoned, which is a continuation-in-part of application No. 12/210,368, filed on Sep. 15, 2008, now abandoned, which is a continuation-in-part of application No. 11/945,674, filed on Nov. 27, 2007, now Pat. No. 7,543,760, said application No. 14/497,657 is a continuation-in-part of application No. 13/065,621, filed on Mar. 25, 2011, now Pat. No. 9,050,401, application No. 15/091,055, which is a continuation-in-part of application No. 14/497,691, filed on Sep. 26, 2014, now Pat. No. 9,662,435, which is a continuation-in-part of application No. 13/857,448, filed on Apr. 5, 2013, now Pat. No. 9,486,594, which is a continuation-in-part of application No. 13/068,680, filed on May 17, 2011, now Pat. No. 8,876,749, which is a continuation-in-part of application No. 12/652,845, filed on Jan. 6, 2010, now abandoned, which is a continuation-in-part of application No. 12/210,368, filed on Sep. 15, 2008, now abandoned, which is a continuation-in-part of application No. 11/945,674, filed on Nov. 27, 2007, now Pat. No. 7,543,760, said application No. 14/497,691 is a continuation-in-part of application No. 13/065,621, filed on Mar. 25, 2011, now Pat. No. 9,050,401, application No. 15/091,055, which is a continuation-in-part of application No. 13/569,444, filed on Aug. 8, 2012, now Pat. No. 9,651,197, which is a continuation-in-part of application No. 13/068,680, filed on May 17, 2011, now Pat. No. 8,876,749, which is a continuation-in-part of application No. 12/652,845, filed on Jan. 6, 2010, now abandoned, which is a continuation-in-part of application No. 12/210,368, filed on Sep. 15, 2008, now abandoned, which is a continuation-in-part of application No. 11/945,674, filed on Nov. 27, 2007, now Pat. No. 7,543,760.

(60) Provisional application No. 60/867,323, filed on Nov. 27, 2006, provisional application No. 61/395,892, filed on May 19, 2010.

(51) Int. Cl.

| | | |
|---|---|---|
| *A61B 5/00* | (2006.01) | |
| *A61M 5/14* | (2006.01) | |
| *A61M 5/145* | (2006.01) | |
| *A61M 5/168* | (2006.01) | |
| *A61M 5/178* | (2006.01) | |
| *A61J 1/22* | (2006.01) | |
| *A61M 5/36* | (2006.01) | |
| *A61M 39/10* | (2006.01) | |
| *F17C 13/00* | (2006.01) | |
| *A61B 8/08* | (2006.01) | |
| *A61K 9/00* | (2006.01) | |
| *A61J 1/20* | (2006.01) | |
| *A61M 25/10* | (2013.01) | |
| *A61M 13/00* | (2006.01) | |
| *A61M 15/08* | (2006.01) | |

(52) U.S. Cl.
CPC ............... *A61J 1/2096* (2013.01); *A61J 1/22* (2013.01); *A61M 5/1407* (2013.01); *A61M 5/1452* (2013.01); *A61M 5/16827* (2013.01); *A61M 5/16881* (2013.01); *A61M 5/178* (2013.01); *A61M 5/36* (2013.01); *A61M 25/10185* (2013.11); *A61M 39/105* (2013.01); *A61M 39/22* (2013.01); *A61M 39/223* (2013.01); *F17C 13/00* (2013.01); *A61B 8/481* (2013.01); *A61J 1/2051* (2015.05); *A61J 1/2089* (2013.01); *A61J 2200/70* (2013.01); *A61K 9/0019* (2013.01); *A61M 13/003* (2013.01); *A61M 15/08* (2013.01); *A61M 25/10186* (2013.11); *A61M 25/10187* (2013.11); *A61M 2005/006* (2013.01); *A61M 2025/102* (2013.01); *A61M 2202/0225* (2013.01)

(56) References Cited

U.S. PATENT DOCUMENTS

| | | |
|---|---|---|
| 3,879,703 A | 4/1975 | Bonazoli et al. |
| 4,744,356 A | 5/1988 | Greenwood |
| 4,786,394 A | 11/1988 | Enzer et al. |
| 4,854,343 A * | 8/1989 | Rilett ............... A62C 13/76 137/543.19 |
| 4,950,230 A | 8/1990 | Kendell |
| 5,135,026 A | 8/1992 | Manske |
| 5,154,348 A | 10/1992 | Ratnik et al. |
| 5,163,909 A * | 11/1992 | Stewart ............. A61M 5/1486 128/DIG. 12 |
| 5,195,963 A | 3/1993 | Yafuso et al. |
| 5,221,113 A * | 6/1993 | Stoll ................. F16B 33/02 285/333 |
| 5,345,932 A | 9/1994 | Yafuso et al. |
| 5,565,215 A * | 10/1996 | Gref ................. A61K 9/0019 424/451 |
| 5,699,961 A | 12/1997 | Ratnik et al. |
| 6,164,556 A | 12/2000 | Dupre et al. |
| 6,295,007 B1 | 9/2001 | O'Meara |
| 6,315,762 B1 | 11/2001 | Recinella et al. |
| 6,402,047 B1 | 6/2002 | Thomas |
| 6,474,091 B2 | 11/2002 | Guerra |
| 6,533,766 B1 * | 3/2003 | Patterson ........... A61L 29/08 427/2.12 |
| 6,572,873 B1 | 6/2003 | Osman et al. |
| 7,543,760 B2 | 6/2009 | Levy et al. |
| 2001/0044618 A1 | 11/2001 | Recinella et al. |
| 2002/0017328 A1 | 4/2002 | Loo |
| 2002/0174578 A1 | 11/2002 | Ross |
| 2003/0181850 A1 | 9/2003 | Diamond et al. |
| 2005/0000981 A1 | 1/2005 | Peng et al. |
| 2005/0119607 A1 | 6/2005 | Van Der Linden et al. |
| 2006/0004322 A1 | 1/2006 | Uesugi et al. |
| 2006/0071091 A1 | 4/2006 | Ratnik |
| 2006/0074386 A1 | 4/2006 | Wollmann |
| 2006/0178620 A1 | 8/2006 | Wollmann |
| 2007/0104616 A1 | 5/2007 | Keenan et al. |
| 2007/0111298 A1 | 5/2007 | Muller et al. |
| 2008/0004549 A1 | 1/2008 | Anderson et al. |
| 2008/0120992 A1 | 5/2008 | Levy |
| 2008/0167621 A1 | 7/2008 | Wagner et al. |
| 2009/0062741 A1 | 3/2009 | Smith et al. |
| 2009/0247985 A1 | 10/2009 | Melsheimer et al. |
| 2009/0318890 A1 | 12/2009 | Levy |
| 2010/0101579 A1 | 4/2010 | Levy |
| 2011/0112041 A1 | 5/2011 | Schiffmann |
| 2011/0152850 A1 | 6/2011 | Niedbala et al. |
| 2011/0218411 A1 | 9/2011 | Keenan et al. |

FOREIGN PATENT DOCUMENTS

| | | |
|---|---|---|
| EP | 2468204 A1 | 6/2012 |
| JP | H06-013845 U | 2/1994 |
| WO | WO00/72821 | 12/2000 |

(56) References Cited

FOREIGN PATENT DOCUMENTS

| WO | WO02/41872 | 5/2002 |
|---|---|---|
| WO | WO2005/048984 | 6/2005 |

\* cited by examiner

DELIVERY SYSTEM AND METHOD FOR THE EFFECTIVE AND RELIABLE DELIVERY OF CONTROLLED AMOUNTS OF A MEDICAL FLUID

CROSS REFERENCE TO RELATED APPLICATIONS

This application is a continuation in part of Ser. No. 14/497,657, entitled "Delivery System For The Effective, Reliable And Foolproof Delivery Of Controlled Amounts Of A Medical Fluid," filed Sep. 26, 2014, which is currently pending, which is continuation in part of U.S. patent application Ser. No. 13/857,448, filed Apr. 5, 2013, entitled "Portable Medical Gas Delivery System", which is currently pending, which is a continuation in part of U.S. patent application Ser. No. 13/068,680, filed May 17, 2011, entitled "Apparatus and Process for Producing CO2 Enriched Medical Foam", which is now U.S. Pat. No. 8,876,749, which is a continuation in part of U.S. patent application Ser. No. 12/652,845, filed Jan. 6, 2010, entitled "Portable Medical Gas Delivery System", which is abandoned, which is a continuation in part of U.S. patent application Ser. No. 12/210,368, filed Sep. 15, 2008, entitled "Portable Medical Foam Apparatus", which is abandoned, which is a continuation in part of U.S. patent application Ser. No. 11/945,674, filed Nov. 27, 2007, entitled "Portable Evaporative Snow Apparatus", now U.S. Pat. No. 7,543,760, which claims the benefit of U.S. Provisional Patent Application Ser. No. 60/867,323, filed Nov. 27, 2006, entitled "Portable Evaporative Snow Apparatus", and U.S. patent application Ser. No. 14/497,657, entitled "Delivery System For The Effective, Reliable And Foolproof Delivery Of Controlled Amounts Of A Medical Fluid," filed Sep. 26, 2014, which is currently pending, is a continuation in part of U.S. patent application Ser. No. 13/065,621, filed Mar. 25, 2011, entitled "System for Controlled Delivery of Medical Fluids", which is now U.S. Pat. No. 9,050,401, which claims the benefit of U.S. Provisional Patent Application Ser. No. 61/395,892, filed May 19, 2010, entitled "System for Controlled Delivery of Medical Fluids";

and this application is a continuation in part of Ser. No. 14/497,691, entitled "Delivery System For The Effective, Reliable And Foolproof Delivery Of Controlled Amounts Of A Medical Fluid," filed Sep. 26, 2014, which is currently pending, which is continuation in part of U.S. patent application Ser. No. 13/857,448, filed Apr. 5, 2013, entitled "Portable Medical Gas Delivery System", which is currently pending, which is a continuation in part of U.S. patent application Ser. No. 13/068,680, filed May 17, 2011, entitled "Apparatus and Process for Producing CO2 Enriched Medical Foam", which is now U.S. Pat. No. 8,876,749, which is a continuation in part of U.S. patent application Ser. No. 12/652,845, filed Jan. 6, 2010, entitled "Portable Medical Gas Delivery System", which is abandoned, which is a continuation in part of U.S. patent application Ser. No. 12/210,368, filed Sep. 15, 2008, entitled "Portable Medical Foam Apparatus", which is abandoned, which is a continuation in part of U.S. patent application Ser. No. 11/945,674, filed Nov. 27, 2007, entitled "Portable Evaporative Snow Apparatus", now U.S. Pat. No. 7,543,760, which claims the benefit of U.S. Provisional Patent Application Ser. No. 60/867,323, filed Nov. 27, 2006, entitled "Portable Evaporative Snow Apparatus", and U.S. patent application Ser. No. 14/497,657, entitled "Delivery System For The Effective, Reliable And Foolproof Delivery Of Controlled Amounts Of A Medical Fluid," filed Sep. 26, 2014, which is currently pending, is a continuation in part of U.S. patent application Ser. No. 13/065,621, filed Mar. 25, 2011, entitled "System for Controlled Delivery of Medical Fluids", which is now U.S. Pat. No. 9,050,401, which claims the benefit of U.S. Provisional Patent Application Ser. No. 61/395,892, filed May 19, 2010, entitled "System for Controlled Delivery of Medical Fluids";

and this application is a continuation in part of U.S. patent application Ser. No. 13/569,444, filed Aug. 8, 2012, entitled "Disposable Cartridge For Holding Compressed Gas", which is currently pending, which is a continuation in part of U.S. patent application Ser. No. 13/068,680, filed May 17, 2011, entitled "Apparatus and Process for Producing CO2 Enriched Medical Foam", which is now U.S. Pat. No. 8,876,749, which is a continuation in part of U.S. patent application Ser. No. 12/652,845, filed Jan. 6, 2010, entitled "Portable Medical Gas Delivery System", which is abandoned, which is a continuation in part of U.S. patent application Ser. No. 12/210,368, filed Sep. 15, 2008, entitled "Portable Medical Foam Apparatus", which is abandoned, which is a continuation in part of U.S. patent application Ser. No. 11/945,674, filed Nov. 27, 2007, entitled "Portable Evaporative Snow Apparatus", now U.S. Pat. No. 7,543,760, which claims the benefit of U.S. Provisional Patent Application Ser. No. 60/867,323, filed Nov. 27, 2006, entitled "Portable Evaporative Snow Apparatus", the disclosures of which are incorporated herein by reference in their entirety.

BACKGROUND OF THE INVENTION

1. Field of the Invention

This invention relates to a portable system for safely and efficiently producing and delivering $CO_2$ and other gases for use in medical applications.

2. Description of the Related Art

Conventional devices for delivering gas such as carbon dioxide ($CO_2$) for use in medical procedures typically utilize large storage tanks and regulators. Such devices are dangerous because of the risk of a seal, valve or part malfunction, which can produce a projectile in a medical setting. In addition, existing tank systems are quite expensive, extremely cumbersome and usually impractical to transport to off-site locations. These systems typically require a considerable amount of storage space. Current tanks also require filling at a filling station, which can involve the transport of a large quantity of gas such as $CO_2$. Pressurized gas tanks can explode in the event of a motor vehicle crash. Re-fellable tanks can also exhibit rust, bacteria and contamination, which are not acceptable in a medical environment.

Still further, various types of medical equipment have been utilized to deliver controlled volumes of liquid and gaseous substances to patients. One field that involves the administration of such fluids is radiology, wherein a small amount of carbon dioxide gas or an alternative contrast media may be delivered to the vascular system of the patient to displace the patient's blood and obtain improved images of the vascular system. Traditionally, this has required that the $CO_2$ or other media first be delivered from a pressurized cylinder to a syringe. The filled syringe is then disconnected from the cylinder and reconnected to a catheter attached to the patient. If additional $CO_2$ is needed, the syringe must be disconnected from the catheter and reattached to the cylinder for refilling Not only is this procedure tedious and time consuming, it presents a serious risk of introducing air into the $CO_2$ or contrast fluid at each point of disconnection.

Injecting such air into the patient's blood vessels can be extremely dangerous and even fatal.

Recinella et al., U.S. Pat. No. 6,315,762 discloses a closed delivery system wherein a bag containing up to 2,000 ml of carbon dioxide or other contrast media is selectively interconnected by a stopcock to either the chamber of a syringe or a catheter attached to the patient. Although this system does reduce the introduction of air into the administered fluid caused by disconnecting and reconnecting the individual components, it still exhibits a number of shortcomings. For one thing, potentially dangerous volumes of air are apt to be trapped within the bag. This usually requires the bag to be manipulated and flushed multiple times before it is attached to the stopcock and ultimately to the catheter. Moreover, this delivery system does not feature an optimally safe and reliable, foolproof operation. If the stopcock valve is incorrectly operated to inadvertently connect the carbon dioxide filled bag or other source of carbon dioxide directly to the patient catheter, a dangerous and potentially lethal volume of $CO_2$ may be delivered suddenly to the patient's vascular system. It is medically critical to avoid such $CO_2$ flooding of the blood vessels.

SUMMARY OF THE INVENTION

It is therefore an object of the present invention to provide a system for safely and reliably delivering a controlled dosage of a fluid to a medical patient.

It is a further object of this invention to provide a fluid (i.e. liquid or gas) delivery system that is particularly effective for use in administering $CO_2$ or other contrast media in a controlled manner to a patient's vascular system to provide improved contrast for radiological imaging.

It is a further object of this invention to provide a fluid delivery system and particularly a $CO_2$/contrast media delivery system that prevents potentially dangerous amounts of air from entering the fluid and thereby being administered to the patient.

It is a further object of this invention to provide a fluid delivery system that prevents accidentally flooding of the patient's vascular system with carbon dioxide or other administered gases or liquids under positive pressure.

It is a further object of this invention to provide a fluid delivery system exhibiting a failsafe and foolproof operation, which permits only reliable and accurately controlled dosages of a medical fluid to be administered to a patient.

It is a further object of this invention to provide a fluid delivery system that may be used safely and effectively with virtually any source of carbon dioxide or other medical fluid regardless of the pressure or environment under which that fluid is maintained.

It is a further object of this invention to provide a fluid flow system that prevents an administered medical fluid from flowing in an unintended direction through the system.

In accordance with these objects, the present invention provides a method for using carbon dioxide as a contrast material in medical imaging procedures. The method includes providing a source of pressurized carbon dioxide, connecting the source of pressurized carbon dioxide to a compressed gas unit including a solenoid for controlling delivery of the carbon dioxide, regulating pressure of the carbon dioxide delivered by the compressed gas unit and transmitting the pressurized carbon dioxide from the compressed gas unit to a control valve assembly for delivery to a patient in controlled dosages. Thereafter, the carbon dioxide is sequentially processed with the control valve assembly and delivered to the patient as a contrast media.

It is also an object of the present invention to provide a method wherein the step of sequentially processing includes delivering carbon dioxide through a series of syringes such that it is impossible to directly connect the compressed gas unit to the patient.

It is also an object of the present invention to provide a method wherein the step of sequentially processing includes providing inlet and outlet conduits connected respectively to the compressed gas unit and the patient. The method also includes providing first and second syringes and the control valve assembly, which are interconnected between the inlet and outlet conduits.

It is also an object of the present invention to provide a method wherein the control valve assembly includes a valve body having aligned inlet and outlet ports that are respectively communicably connectable to the inlet conduit and the outlet conduits. The valve body further includes a first intermediate port to which the first syringe is selectively connected and a second intermediate port to which the second syringe is selectively connected. The control valve assembly further includes a stopcock element mounted rotatably within the body and including a channel consisting essentially of a first channel segment and a second channel segment. The first channel segment and the second channel segment are selectively alignable with the inlet port and the first intermediate port to allow for communication between the inlet conduit and the first syringe. The first intermediate port and the second intermediate port allow for communication between the first syringe and the second syringe, and the second intermediate port and the outlet port to allow for communication between the second syringe and the outlet conduit.

It is also an object of the present invention to provide a method wherein the step of sequentially processing includes operating the control valve assembly to communicably join the compressed gas unit and the first syringe and transmitting carbon dioxide from the compressed gas unit to only the first syringe, adjusting the control valve assembly to communicably join the first and second syringes while isolating the first syringe from the compressed gas unit, operating the first syringe to transmit carbon dioxide from the first syringe to only the second syringe through the control valve assembly, adjusting the control valve assembly to communicably join the second syringe to the outlet conduit and to isolate the first syringe and the compressed gas unit from the second syringe, and operating the second syringe to transmit carbon dioxide from the second syringe to only the patient through the outlet conduit.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
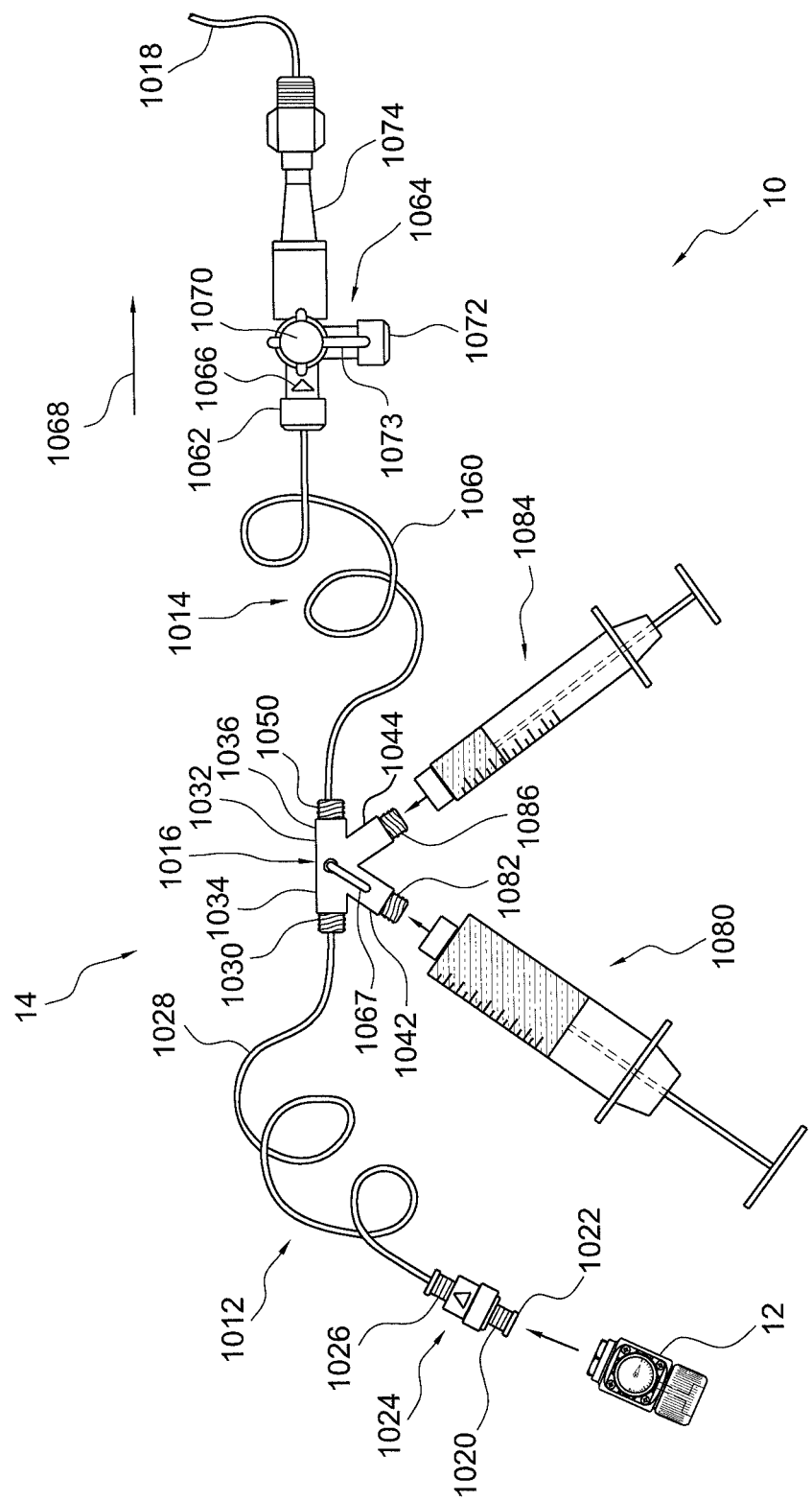
FIG. 1 is a schematic of a delivery system in accordance with the present invention.

Referring to the various figures, and in particular FIG. 1, the present invention provides a delivery system 10 for the effective, reliable and foolproof delivery of controlled amounts of a medical fluid such as $CO_2$ or other contrast media to a patient. In accordance with the present invention, delivery is achieved through the utilization of an integrated compressed gas unit 12 and a multi-part valve delivery system 14. The multi-part valve delivery system 14 delivers the fluid in precisely controlled amounts sequentially through a series of syringes such that it is impossible to directly connect the fluid source to the patient. At the same time, the delivery system 10 does not have to be disconnected and reconnected during the administration of medical fluid. This greatly reduces the intrusion of air into the system and the fluid being administered.

Figure 2:
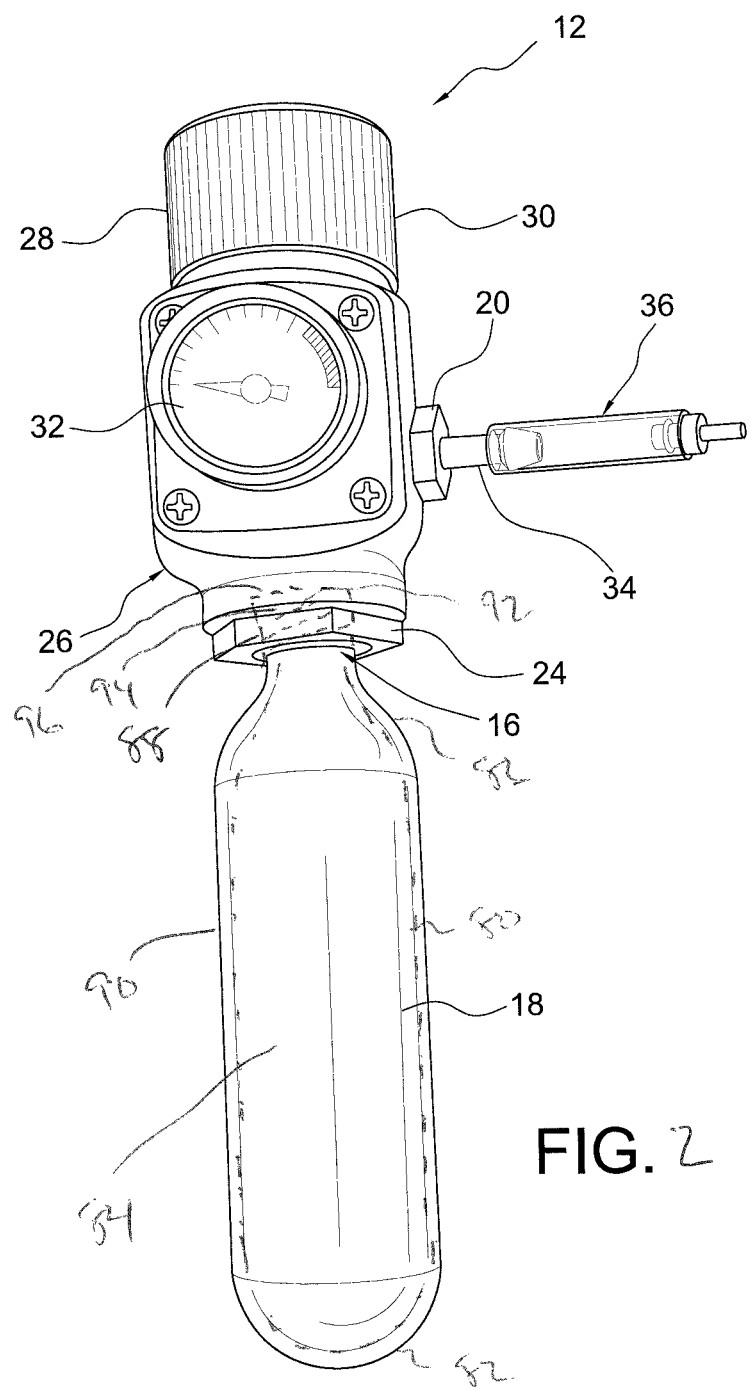
FIG. 2 is a perspective view of the compressed gas unit with a capsule secured thereto.
Figure 3:
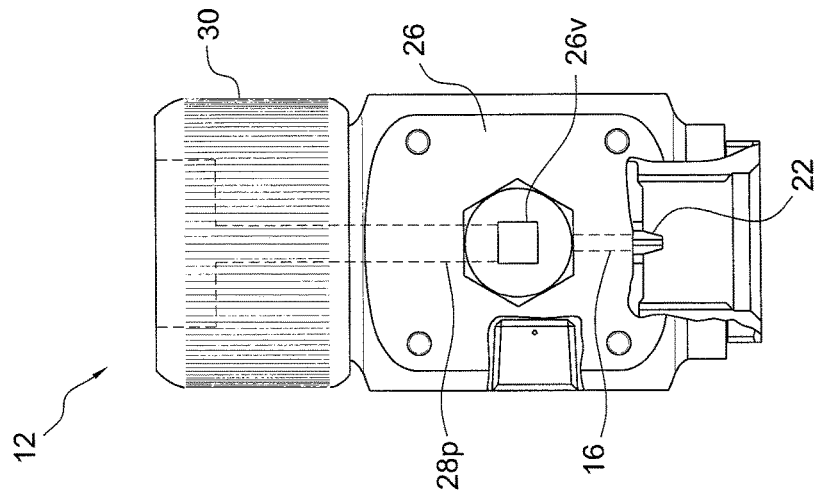
FIG. 3 is a front plan view of the compressed gas unit shown in FIG. 2.
Figure 4:
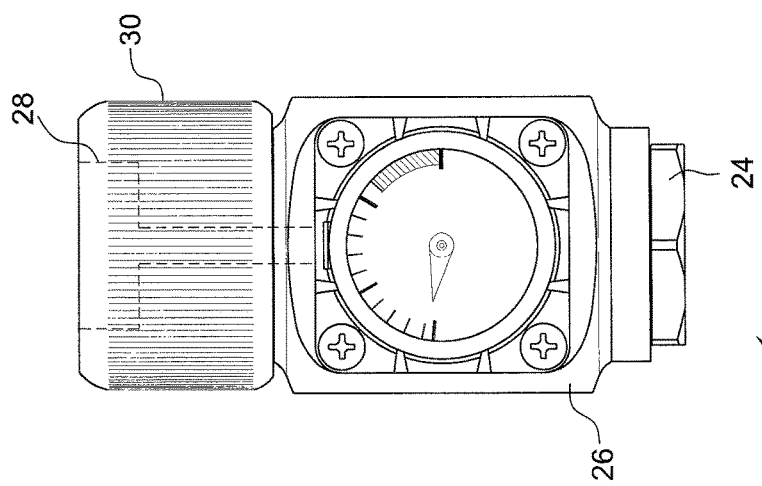
FIG. 4 is a side plan view of the compressed gas unit shown in FIG. 2.

With reference to FIGS. 2-4, the integrated compressed gas unit 12 is disclosed. The integrated compressed gas unit 12 includes an inlet port 16 to which at least one compressed gas ($CO_2$) cylinder 18 is selectively connected and an outlet port 20 in communication with the inlet port 16, and ultimately the at least one compressed gas ($CO_2$) cylinder 18.

The compressed gas cylinder 18 is secured to, and maintained in fluid communication with, the integrated compressed gas unit 12 by a cylinder cartridge puncture valve 22 and a fitting 24 formed at the inlet port 16 of the integrated compressed gas unit 12. In accordance with a preferred embodiment, the cylinder cartridge puncture valve 22 has a mechanism for piercing the compressed gas cylinder 18, as is known in the art, and for holding or securing the compressed gas cylinder 18 in place.

The compressed gas exits the inlet port 16 and passes through a regulator valve assembly 26 controlled by a press button actuator 28 and regulator adjustment dial 30. The regulator valve assembly 26 dictates the pressure of the gas as it ultimately exits the outlet port 20. In accordance with a preferred embodiment, the regulator valve assembly 26 has a selective outlet pressure in the range of 7 psi to 19 psi. The outlet pressure is achieved by rotating the regulator adjustment dial 30 of the button actuator 28. In addition, to regulating the applied pressure, the regulator valve assembly 26 also includes a valve 26v that controls the passage of gas from the inlet port 16 to the outlet port 20. The valve 26v is controlled via a push button mechanism 28p in the button actuator 28 such that a user may selectively determine when gas may pass therethrough to the outlet port 20. In accordance with a preferred embodiment, the $CO_2$ flow rate is less than 12 NL/min.

As mentioned above, the regulator valve assembly 26 also includes a regulator adjustment dial 30 which controls the pressure permitted to exit the outlet port 20 by either rotating the regulator adjustment dial 30 clockwise or counterclockwise as may be desired to adjust the applied pressure. The applied pressure may be monitored using the PSI gauge formed on the front face 32 of the integrated compressed gas unit 12.

In practice, a compressed gas cylinder 18 is applied to the integrated compressed gas unit 12 in the following manner. The adjustment dial 30 is first disengaged (loosened) by rotating the same in a counter-clockwise direction. The compressed gas cylinder 18 is then screwed into the fitting 24 and the cylinder cartridge puncture valve 22 punctures compressed gas cylinder 18. The system is then actuated as by engaging the adjustment dial in a clockwise direction and operating the same as described above through the manipulation of the press button actuator 28 and the adjustment dial 30.

As mentioned above, the outlet port 20 is in fluid communication with the inlet port 16 for transport of gas in accordance with the present invention. The outlet port 20 is provided with a luer connection 34 for the secure and selective attachment of an outlet tube 36 thereto.

Figure 5:
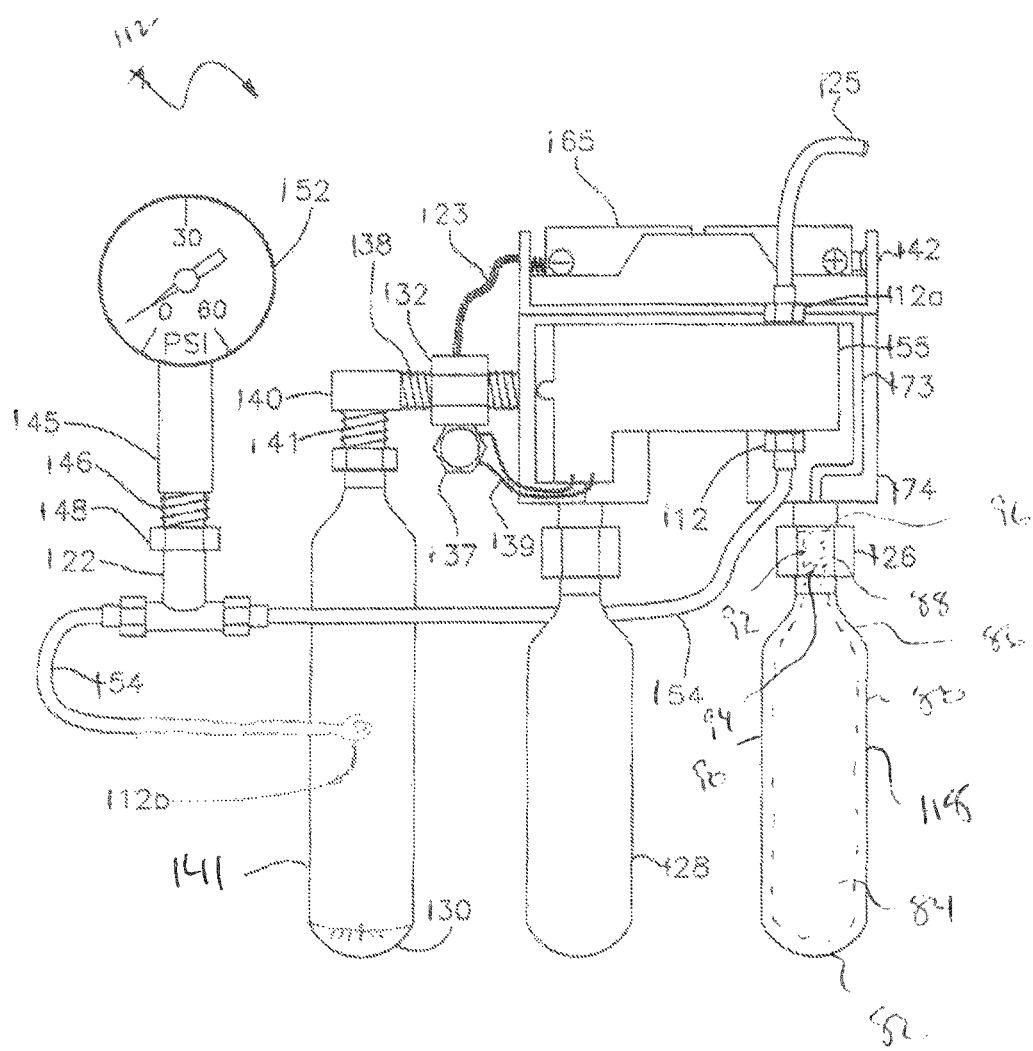
FIG. 5 is a schematic of a compressed gas unit in accordance with an alternate embodiment.

Referring now to FIG. 5, an alternate embodiment of a compressed gas unit 112 in accordance with the present invention is disclosed. The compressed gas unit includes a solenoid 155 with at least one compressed gas (CO) cylinder 118 connected communicably to the solenoid 155. The compressed gas cylinder 118 is secured into position to the compressed gas unit 112 by means of cylinder cartridge puncture valve 126 and a fitting 174. In a preferred embodiment, the cylinder cartridge puncture valve 126 has a mechanism for piercing the cylinder 118, as is known in the art, and for holding or securing the cylinder 118 in place. Compressed air is delivered to the solenoid 155 from the compressed gas cylinder 118 through the cylinder cartridge puncture valve 126 and the conduit 173 of the fitting 174. The conduit 173 of the fitting 174 communicates with a threaded conduit 138 described more fully below.

The compressed gas unit 112 has at least one battery 165 held in place by a battery holder 142, for providing electrical power by which the solenoid 155 may be selectively activated and opened by a pressure activation switch or activation switch 137. The activation switch 137 is designed so that the solenoid 155 is opened when a physician or other medical personnel engages the activation switch 137 by voluntarily applying a small predetermined amount of fingertip pressure to the activation switch 137. It is not activated by a breathing sensor or other actuators designed to be operated by involuntary movement of the user's body. The battery 165 supplies power to the solenoid 155 through a switch wire assembly 123, which is connected to the activation switch 137. The activation switch 137 is mounted to a pressure nut 132 carried on threaded conduit 138. The compressed gas unit 112 has electrical wiring 139 for providing necessary electricity from the activation switch 137 to the solenoid 155.

The compressed gas unit 112 also comprises a separate black rock regulator 143, which is distinct from the solenoid 155. The black rock regulator 143 is controlled or adjusted by a regulator adjustment knob 130 to provide a selected level of pressure to the gas provided to the solenoid 155. The black rock regulator 140 is communicably connected to the compressed gas unit 112 by an elbow pipe 140. The elbow pipe 140 includes a threaded vertical conduit segment 141 joined to the black rock regulator 143 through a connector nut and the threaded horizontal conduit 138, which is engaged by pressure nut 132.

As discussed above, the compressed gas cylinder 118 is secured to the compressed gas unit 112 by the cartridge puncture valve 126 as is commonly known. In one embodiment, the compressed gas cylinder 118 is a 25 gram cylinder. Alternative capacities (e.g. 16, 36, 45 grams) may be used within the scope of this invention. Compressed air leaves the black rock regulator 143 at the regulator adjusted pressure through a $^{10}/_{32}$" hose port 113b and flows through a hose junction 122, by means of a $^{1}/_{8}$" pressure hose 154, until reaching the $^{10}/_{32}$" hose port 113a affixed to the solenoid 155. From the hose port 113a, the compressed air enters the solenoid 155. The compressed air unit 112 also has an outlet air port 125, which is connected to the solenoid 155 through intermediate $^{10}/_{32}$" hose port 113a for transporting compressed gas, namely CO2 from the solenoid 155 in the compressed gas unit 112 to the flow control system when the solenoid 155 is opened. Outlet gas may be monitored with a pressure gauge 152 connected to the hose junction 122 through a conduit 145 having threads 146. The threaded end of the conduit 145 interengages a nut 148 carried by the hose junction 122.

In certain embodiments a second compressed gas cylinder or cartridge 128, featuring a 16 g or 25 g compressed gas cylinder, may be used in addition to or in lieu of the primary gas cylinder 118. In still other embodiments, a larger compressed gas cylinder and expansion chamber may be substituted for the gas cartridges previously described in accordance with the invention. The size and number of compressed gas containers are not limitations of the invention.

Figure 6:
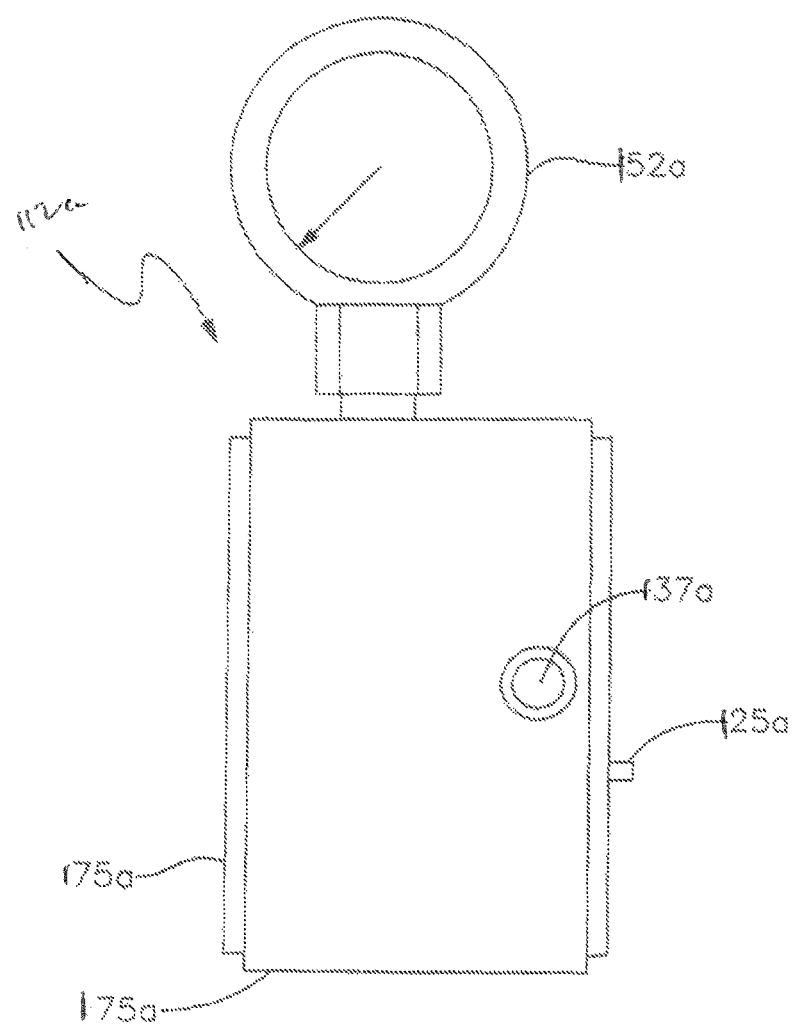
FIG. 6 is a schematic front view of an alternative compressed gas unit enclosed in a housing.
Figure 7:
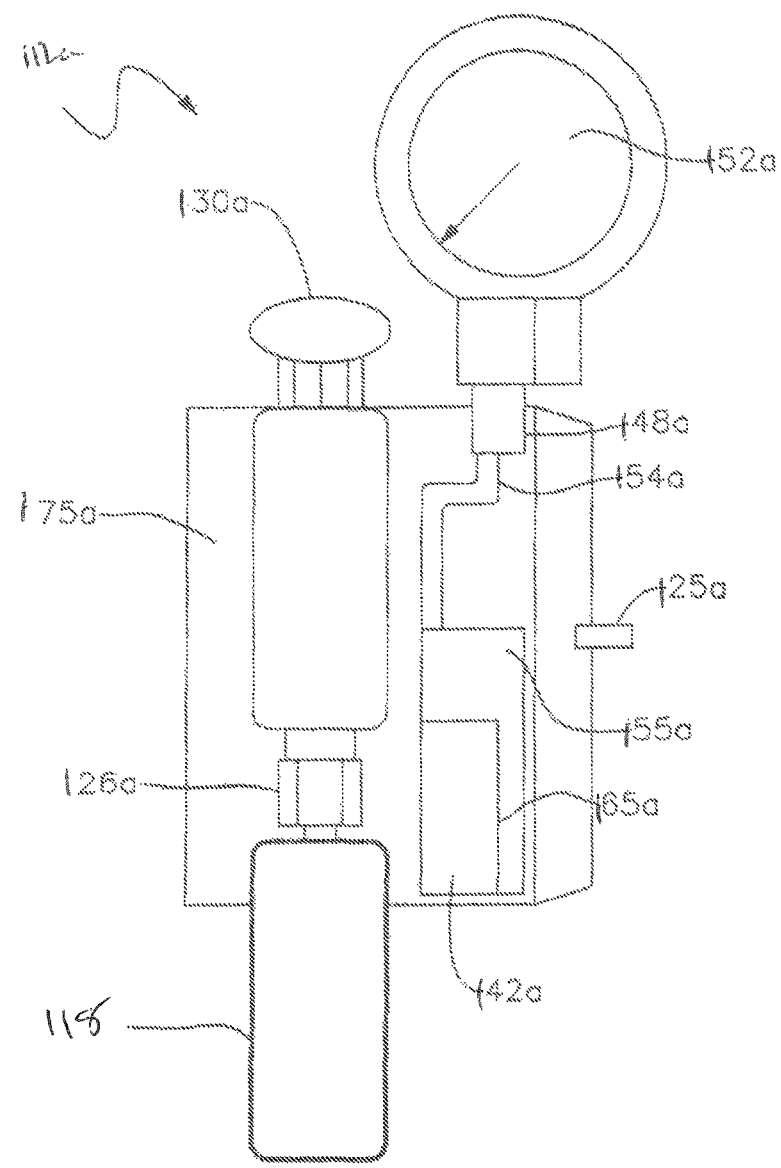
FIG. 7 depicts a schematic layout of the components of the compressed gas unit of FIG. 2.

FIGS. 6 and 7 depict an alternative embodiment of a compressed gas unit 112a wherein venous components of the gas unit 112a are enclosed in a housing 175a. The components of the compressed gas unit 112a are designated by reference numerals that correspond to those of the previously described embodiment and further include lower case "a" designations. In particular, a $CO_2$ cartridge 118a is connected by a puncture valve 126a to a regulator 143a. The regulator is controlled by an adjustment knob 130a. The regulator 143a is connected through a conduit 154a to both a pressure gauge 152a and a solenoid 155a. More particularly, the pressure gauge 152a is connected to a coupling 148a. The solenoid 155a is powered by a battery 165a, which is itself held in place within the housing by a holder 142a. A user accessible Luer fitting 125a is communicably connected to the solenoid 155a and extends exteriorly of the housing 175a.

The compressed gas unit 112a is activated to selectively open the solenoid 155a by manually engaging the switch 137a through voluntary fingertip pressure. This transmits the pressure regulated $CO_2$ or other gas through the solenoid 155a and the fitting 125a. The compressed gas unit 112a thereby operates in a manner analogous to that previously described to provide pressure adjusted $CO_2$ from the cartridge 118a through the Luer fitting 125a to the flow control system or other destination for the medical gas. The following are preferred examples of such applications.

As briefly mentioned above, the compressed gas cylinder 18, 118 is secured to the compressed air unit 12, 112 by a cartridge puncture valve 22, 126 as is commonly known. In accordance with one embodiment, the compressed gas cylinder 18 is a 25 g cylinder. Alternative capacities (e.g. 16, 36, 45 grams) may be used within the scope of this invention. Compressed air leaves the regulator valve assembly 26 at the regulator adjusted pressure and goes to the outlet port 20. The compressed gas cylinder is a single use gas supply prepared specifically for the purpose of medical procedures. This overcomes contamination issues and provides for the knowledge that the procedure is being performed in a sanitary and safe manner Knowledge of the sources of contamination and how to avoid them is imperative but relatively simple. During the inception of intravascular use of $CO_2$, Hawkins found that routine, reusable cylinders contained carbonic acid, rust, particulate matter and water. Hawkins I F, Caridi J G. *Carbon dioxide (CO2) digital subtraction angiography: 26 year experience at the University of Florida. Eur Radiol.* 1998; 8(3):391-402. It is essential, therefore, that disposable sources of at least medical-grade $CO_2$ be utilized. The present invention provides for the use of research grade $CO_2$, which is more pure and provides for safe procedures with no need to worry about contamination. Not only does this avoid inappropriate embolization but it also avoids pain for the patient.

Referring to FIGS. 2 and 5, the compressed gas cylinder 18, 118 is composed of a disposable aluminum cartridge accommodating a compressed medical gas. It should be understood that cartridge is suitable for holding a wide variety of medical gases including, but not limited to, carbon dioxide, oxygen and nitrous oxide. Cartridge is capable of holding virtually any type of medical gas in a pressurized condition for use in various types of medical procedures. The type of gas and the type of medical applications involved are not limitations of this invention.

The cartridge 18, 118 includes a generally cylindrical canister body 80, 180 having an elongate shape with a rounded bottom 82, 182. The canister body 80, 180 encloses an interior chamber 84, 184 for holding a compressed medical gas. The canister body 80, 180 includes a tapered neck portion 86, 186 that is joined to and terminates in a reduced diameter cylindrical end portion 88, 188. The canister body 80, 180, tapered neck portion 86, 186 and reduced diameter cylindrical end portion 88, 188 thereby define a canister 90, 190 that is preferably composed of aluminum. The cylindrical end portion 88, 188 is preferably encircled by a thread 92, 192 that allows the canister 90, 190 to be screwed into a complementary threaded opening of a piece of the compressed gas unit 12, 112. The optimum thread size is $^{3}/_{8}$" although it can vary from $^{1}/_{4}$ to 1" within the scope of this invention.

In radiological applications, the canister 90, 190 is used to hold carbon dioxide in the chamber 84, 184 and the threaded reduced diameter cylindrical end portion 88, 188 may be engaged with the portable medical gas delivery system produced under the trademark $CO_2$Mmander® as disclosed in U.S. patent application Ser. Nos. 13/068,880 and 12/652, 845, the disclosures of which are incorporated herein by reference. Although the cartridge is particularly convenient and effective for use with this system, it may be used in a wide variety of other medical applications and for holding venous other types of compressed medical gases.

Reduced diameter cylindrical end portion 88, 188 includes an opening 94, 194 in communication with interior chamber 84, 184. The distal end of reduced diameter cylindrical end portion 88, 188 of the canister 90, 190 carries a pierceable tip 96, 196 that seals opening 94, 194 after pressurized medical gas has been introduced into the interior of canister 90, 190. The tip 96, 196 may comprise a fairly thin and flexible foil that is securely sealed over opening 94, 194 in the cylindrical end portion 88, 188. The tip 96, 196 is readily punctured in a conventional manner to open canister 90, 190 so that compressed gas within the canister 90, 190 is made available for delivering through opening 94, 194 to a desired medical application or use.

The canister 90, 190 is composed and constructed to provide significant advantages. In particular, the canister 90, 190 has a relatively compact size and configuration and is extremely lightweight especially when compared with standard full-sized tanks conventionally used to contain compressed medical gases. In particular, the preferred weight of canister 90,190 is 25 grams, although it can range from 12 to 50 grams. The canister 90, 190 employs a triple-washed aluminum construction, which maintains the sterility and purity of gases contained within the canister 90, 190. In particular, the triple-washed canister 90, 190 resists the formation of mold and rust, as well as the collection of other types of debris within the interior chamber 84, 184 of the canister 90, 190. As a result, the integrity of the canister 90, 190 is maintained so that the contained gas is suitable for medical use wherein nigh levels of purity and sterility are indispensable.

The compact and relatively small size of the cartridge allows the cartridge to be transported and manipulated easily and conveniently. Replacement and disposal of the cartridge are facilitated. Bulky, heavy and cumbersome tanks are avoided.

The compact cartridge is disposable and therefore does not have to be refilled or cleaned between uses. This reduces the time, logistic complexity and tedium required to transport and refill conventional tanks. It also helps to maintain the sterility and purity of the compressed medical gas contained within the cartridge. The lightweight, disposable aluminum cartridge disclosed herein therefore provides for a number of significant advantages over the large bulky and cumbersome tanks used in the prior art.

From the foregoing it may be seen that the apparatus of this invention provides for a disposable aluminum cartridge for accommodating compressed medical gases such as carbon dioxide, oxygen, nitrous oxide and the like.

As briefly mentioned above, the system relies upon the both the compressed gas unit 12 and a multi-part valve delivery system 14 to achieved controlled delivery of $CO_2$. The multi-part valve delivery system 14, which includes a flow control system 1010 as discussed below in greater detail, results from a realization that an improved, foolproof mechanism for safely delivering controlled amounts of a medical fluid such as $CO_2$ or other contrast media to a patient may be accomplished by utilizing a multi-part valve assembly that delivers the fluid in precisely controlled amounts sequentially through a series of syringes such that it is impossible to directly connect the fluid source to the patient. At the same time, the delivery system does not have to be disconnected and reconnected during the administration of medical fluid. This greatly reduces the intrusion of air into the system and the fluid being administered.

For years, it has been reported that the patient should never be connected directly to a source of compressed gas. However, the multi-part valve delivery system 14 obviates this problem since the multi-part valve delivery system 14 precludes the possibility of $CO_2$ passing directly from the source of compressed gas, in this case, a single does compressed cylinder. As will be appreciated based upon the present disclosure, the present delivery systems employs a compact compressed gas unit 12 that uses a small 10,000-cc canister of pharmaceutical-grade $CO_2$. Such a smaller system can be placed in a sterile sleeve or left beneath the sterile drape. By connecting the multi-part valve delivery system 14 between the compressed gas cylinder and the patient, direct communication with the patient is prevent. As will be explained below, the $CO_2$ is introduced into a reservoir syringe (that is, the first syringe 1080 as discussed below). From the reservoir syringe, the gas should be pushed, not aspirated, to the delivery syringe (that is, the second syringe 1084 as discussed below) to avoid the unlikely possibility of air contamination through the control valve assembly 1016. Equilibrium with the atmosphere can be achieved with a 3-way stopcock on the delivery catheter. The system does not require assembly and is extremely user friendly. Set-up for use takes approximately 1 minute. The multi-part valve delivery system 14 provides for controlled delivery of a medical fluid from a source of such fluid to a patient. As will be explained below in greater detail, the multi-part valve delivery system 14 includes an inlet conduit 1012 that is communicably joined to a source of the medical fluid via the compressed gas unit 12 and an outlet conduit 1014 that is communicably joined to the patient. First and second syringes 1080, 1084 are intermediate the inlet and outlet conduits 1012, 1014. A control valve assembly 1016 interconnects the inlet and outlet conduits 1012, 1014 as well as the intermediate first and second syringes 1080, 1084. The control valve assembly 1016 is alternatable between first, second, and third states. In the first state, the inlet communicates with the first syringe 1080 for transmitting fluid from the source to the first syringe 1080. In the second state, the first syringe 1080 communicates with the second syringe 1084 and is isolated from the inlet and the outlet conduits 1012, 1014 for transmitting fluid from the first syringe 1080 to the second syringe 1084. In the third state, the second syringe 1084 communicates with the outlet conduit 1014 and is isolated from the inlet conduit 1012 and the first syringe 1080. This allows fluid to be transmitted from the second syringe 1084 to the patient through the outlet conduit 1014.

In one embodiment, the control valve assembly includes a valve body having aligned inlet and outlet passageways that are communicably connectable to the inlet and outlet conduits respectively. The valve body further includes a pair of first and second transverse passageways that extend axially transversely to the inlet and outlet passageways and transversely to each other. A stopcock is mounted rotatably within the valve body and includes an angled channel having a pair of communicably interconnected channel segments that extend axially at an acute angle to one another. The channel segments of the stopcock are interconnected at an angle that is generally equivalent to the angle formed between each adjacent pair of non-aligned passageways in the valve body such that the stopcock is rotatable to align the channel segments with a selected adjacent pair of the non-aligned passageways to permit fluid communication between those passageways. Each of the transverse passageways is connectable to a respective syringe. The stopcock is selectively adjusted between first, second and third positions. In the first position, the channel segments communicably interconnect the inlet passageway and a first one of the transverse passageways. Fluid introduced through the inlet conduit portion is thereby transmitted through the inlet passageway and the channel of the stopcock to the first transverse passageway. This passageway directs the fluid to a first syringe attached thereto. In the second valve position, the stopcock aligns the channel segments with the first and second transverse passageways respectively. This isolates the fluid in the first syringe from both the inlet and outlet conduits. The first syringe is operated to direct the fluid through the first transverse passageway, the stopcock channel and the second transverse passageway into a second syringe joined to the second transverse passageway. In the third valve position, the stopcock is rotated to align the channel segments with the second transverse passageway and the outlet passageway respectively. This isolates the fluid in the second syringe from the fluid source, the inlet passageway and the first transverse passageway. The second syringe is then operated to drive the fluid through the second transverse passageway, the channel of the stopcock and the outlet passageway to the outlet conduit. The outlet conduit directs this fluid to the patient.

Figure 8:
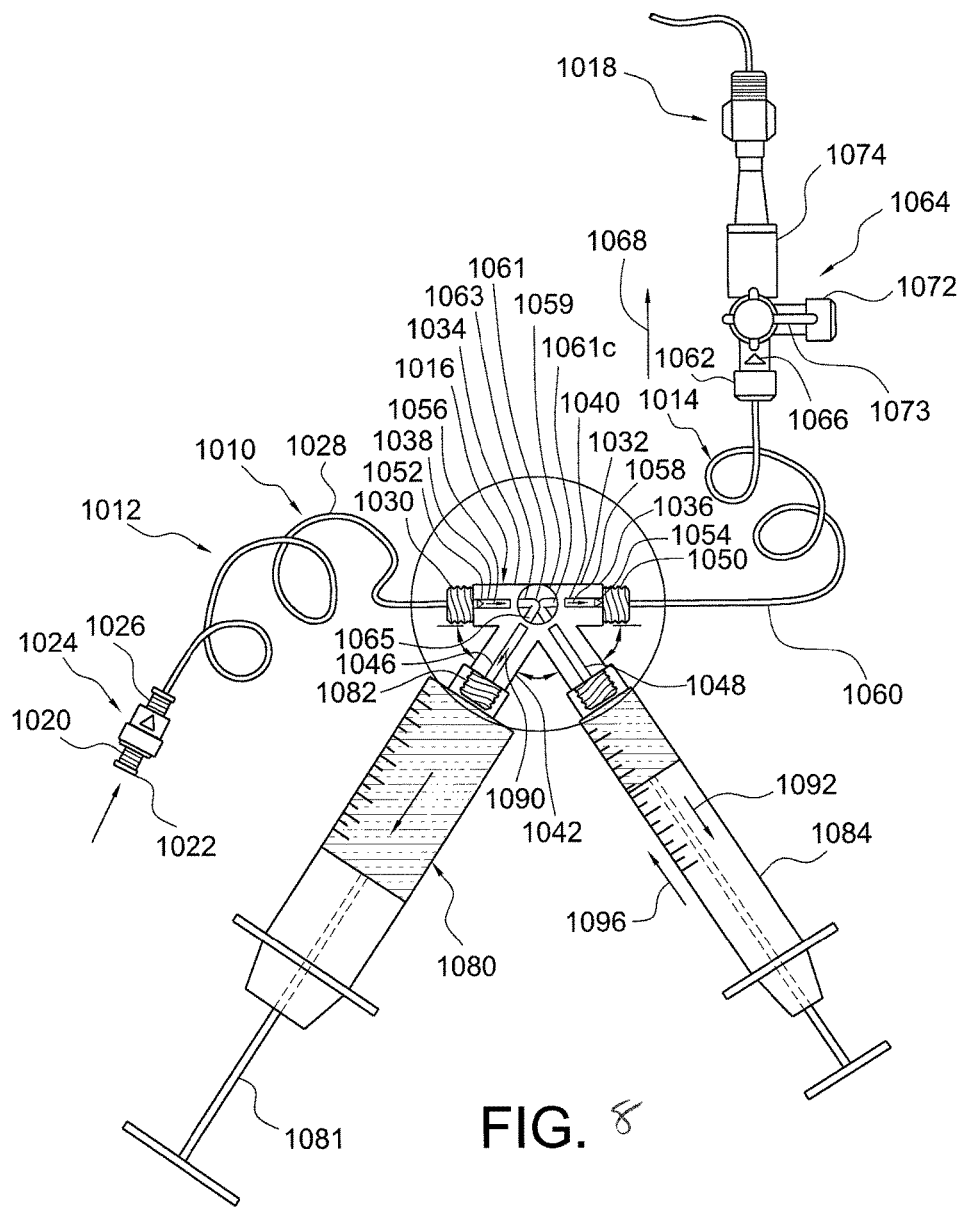
FIG. 8 is a view similar to FIG. 1 wherein the control valve assembly is enlarged for clarity and the internal construction of the valve assembly is illustrated.

There is shown in FIGS. 1 and 8 the flow control system 1010 for delivering controlled dosages of a medical contrast fluid such as carbon dioxide ($CO_2$) for use in the radiological imaging of arteries and veins of a patient's vascular system. Although this is a preferred application for the flow control system 1010, it should be understood that the flow control system 1010 may be used for the controlled delivery of various other types of liquids and gases administered as part of assorted surgical and medical procedures. As used herein, the term "fluid" should be understood to include various types of medical liquids and gases. By the same token, when "gas" is used herein, it should be understood that such description is likewise applicable to various types of medical liquids.

The flow control system 1010 includes an inlet conduit 1012 and an outlet conduit 1014 interconnected by a three-stage K-valve shaped control valve assembly 1016. The inlet conduit 1012 communicably interconnects a source of carbon dioxide from the compressed gas unit 12, 112 with the control valve assembly 1016. The outlet conduit 1014 likewise communicably interconnects a discharge end of the control valve assembly 1016 with a catheter 1018 that is, in turn, operably connected to a patient, not shown.

The inlet conduit 1012 includes a Luer fitting 1020 having a G-tube seal 1022, which is selectively attached to the source of medical fluid, such as the $CO_2$ source. It should be understood that flow control system 1010 may be used with various sources of carbon dioxide including, but not limited to, pressurized tanks, bags and the $CO_2$Mmander® manufactured by PMDA, LLC of North Fort Myers, Fla., which is described above with reference to FIGS. 1 to 3. A one-way directional valve 1024 with a Luer fitting 1026 is communicably joined to the fitting 1020. The Luer™ Fitting 1026 is, in turn, communicably joined to a coiled medical tube 1028 having a length of approximately 18 inches. Various alternative lengths may be employed within the scope of this invention. The distal end of the tube 1028 carries a Luer fitting 1030.

The three-stage control valve assembly 1016 includes a generally K-shaped valve body 1032, which is preferably composed of various medical grade plastics, metals and/or metal alloys. Typically, the valve body 1032 includes a molded or otherwise unitary construction. More particularly, the valve body 1032 includes aligned intake and discharge branches 1034 and 1036, respectively, which, as best shown in FIG. 8, include respective aligned internal passageways 1038, 1040. The valve body 1032 also includes first and second transverse legs 1042, 1044. Each leg 1042, 1044 extends at an angle of substantially 60 degrees from aligned intake and discharge branches 1034, 1036 of the valve body 1032. The first leg 1042 includes an interior passageway 1046 and the second leg 1044 includes an interior passageway 1048, which extend axially longitudinally through the respective first and second legs 1042, 1044. The passageways 1046, 1048 form angles of substantially 60 degrees apiece with the respective axial passageways 1038, 1040 of the aligned intake and discharge branches 1034, 1036. The transverse first and second legs 1042, 1044 also extend at an angle of substantially 60 degrees to one another. By the same token, the longitudinal axes of the passageways 1046, 1048 form an angle of substantially 60 degrees.

The control valve assembly 1016 further includes a stopcock 1059 that, best shown in FIGS. 1 and 8, which is rotatably mounted within valve body 1032. The stopcock 1059 includes an angled channel 1061 comprising communicably interconnected channel segments 1063, 1065 having respective longitudinal axes that extend at an angle of approximately 60 degrees to one another. As used herein, "approximately 60 degrees" should be understood to mean that the angle formed between the respective longitudinal axes of the channel segments 1063, 1065 is substantially equivalent to the angle formed between the longitudinal axes of respective pairs of the non-aligned adjacent passageways of valve body 1032 (e.g. respective pairs of passageways 1038, 1046; 1046, 1048; and 1048, 1040). This enables the channel segments 1063, 1065 to be communicably aligned with a selected pair of the passageways in the manner described more fully below. It should be understood that in alternative embodiments the passageways and channel segments may have other corresponding angles. This is particularly applicable when the intake and discharge passageways and/or the inlet and outlet conduits are not aligned.

As shown in FIGS. 1 and 8, a valve lever 1067 is mounted to the valve body 1032 for selectively rotating the stopcock 1059 into a selected one of three positions. For example, the stopcock 1059 is positioned with channel segments 1063, 1065 of angled channel 1061 communicably aligned with adjacent passageways 1038, 1046, respectively (see FIG. 9A). Alternately, and as described more fully below, the lever 1067 may be manipulated to align the channel segments 1063, 1065 with respective passageways 1046, 1048 as indicated by the channel shown in phantom in position 1061b (see FIG. 9B). The lever 1067 may be likewise operated to align the respective channel segments 1063, 1065 with passageways 1048, 1040 as indicated by the angled channel 1061 in position 1061c (see FIG. 9C). Such selective positioning of the stopcock 1059 provides for controlled multiple stage delivery of fluid through the control valve assembly 1016 from the inlet conduit 1012 to the outlet conduit 1014. This operation is described more fully below.

The intake branch 1034 of the valve body 1032 carries a complementary fitting for communicably interconnecting to the Luer fitting 1030 carried at the distal end of the tubing 1028. By the same token, the discharge branch 1036 of the valve body 1032 carries a complementary fitting for operably and communicably interconnecting with a Luer fitting 1050 carried at the proximal end of the outlet conduit 1014. The remaining elements of the discharge conduit are described more fully below. Aligned passageways 1038 and 1040 of the valve body 1032 include respective one-way valves 1052 and 1054, which restrict or limit the flow of fluid within the respective passageways 1038 and 1040 to the direction indicated by arrows 1056 and 1058.

As further illustrated in FIGS. 1 and 8, the outlet conduit 1014 features a coiled medical tube 1060 that is communicably interconnected between the Luer fitting 1050 attached to the discharge branch 1036 of the valve body 1032 and a second Luer fitting 1062, which is communicably joined to a downstream valve 1064. The downstream valve 1064 includes a one-way valve 1066 that restricts fluid flow from the tubing 1060 through the valve 1064 to the direction indicated by arrow 1068. The valve 1064 features a G-tube seal 1073 that prevents air from intruding into the system prior to connection of the valve 1064. The valve 1064 also includes a stopcock 1070 that is rotatably operated within the valve 1064 to selectively bleed or purge fluid from the flow control system 1010 through a port 1072. Exit port 1074 is selectively joined to patient catheter 1018. Various alternative two and three port stopcocks may be used in the downstream valve.

A reservoir syringe 1080 is communicably connected to axial passageway 1046 of the first valve leg 1042. Such interconnection is accomplished by a conventional Luer fitting 1082, the details of which will be known to persons skilled in the art. Similarly, a second, draw-push syringe 1084 is releasably attached by a Luer fitting 1086 to the distal end of the second valve leg 1044. This allows the second syringe 1084 to be communicably interconnected with the passageway 1048 through the second transverse leg 1044. The first and second syringes 1080 and 1084 are constructed and operated in a manner that will be known to persons skilled in the art.

The flow control system 1010 is operated to deliver $CO_2$ or other medical fluid to a patient in a controlled and extremely safe and reliable manner. This operation is performed as follows.

The inlet conduit 1012 is first interconnected between a source of carbon dioxide via the compressed gas unit 12, 112 and the intake branch 1034 of the valve body 1032. The outlet conduit 1014 likewise is communicably interconnected between the discharge branch 1036 of the valve body 1032 and the downstream valve 1064, which is itself attached to the patient catheter 1018. The first and second syringes 1080 and 1084 are joined to the first and second valve legs 1042 and 1044 such that the first and second syringes communicate with the respective passageways 1046 and 1048. The syringes should be selected such that they have a size that accommodates a desired volume of gas to be administered to the patient during the radiological imaging or other medical/surgical procedure.

After multistage K-control valve assembly 1016 has been interconnected between the inlet and outlet conduit 1012 and 1014, and following attachment of the syringes 1080 and 1084 to the respective valve legs 1042 and 1044, the stopcock 1059 is operated by the valve lever 1067 to align the legs 1063 and 1065 of the stopcock channel 1061 with the valve passageways 1038 and 1046 respectively (see FIG. 8). The source of $CO_2$ is then opened or otherwise operated as required to deliver gas through the inlet conduit 1012 to the control valve assembly 1016. More particularly, and with reference to FIGS. 8 and 9A, the gas is delivered through the one-way valve 1024 and the tubing 1028 to the inlet passageway 1038. The one-way valve 1052 prevents backflow of gas into the coil tubing 1028. The $CO_2$ proceeds in the direction indicated by arrow 1056 and is transmitted through the angled stopcock channel 1061 into the passageway 1046 of the first valve leg 1042. From there, the gas proceeds as indicated by arrow 1090 through the fitting 1082 and into the reservoir first syringe 1080. The $CO_2$ is introduced into the reservoir first syringe 1080 in this manner until it fills the syringe.

When the reservoir first syringe 1080 is filled, the operator manipulates lever 1067, FIG. 1, and rotates the control valve into the second stopcock channel position represented in phantom by 1061b in FIG. 8 (and as shown in FIG. 9B). In that position, the channel segment 1063 is communicably aligned with the passageway 1046 and the channel segment 1065 is communicably aligned with the passageway 1048. The plunger 1081 of the reservoir first syringe 1080 is pushed and the gas previously deposited into the reservoir first syringe 1080 is transmitted through the passageway 1046 and the angled stopcock channel 1061b into the passageway 1048. From there, the gas is introduced into draw-push syringe 1084 as indicated by arrow 1092. As this operation occurs, only the transverse passageways and their attached syringes are communicably connected. Both syringes 1080, 1084 remain completely isolated from both the inlet passageway 1038 and the discharge passageway 1040. By the same token, the source of carbon dioxide and communicably joined intake passageway 1038 are isolated from the discharge passageway 1040 and the outlet conduit 1014 connected to the catheter 1018. The patient is thereby safely protected against being inadvertently administered a dangerous dosage of carbon dioxide directly from the source.

Figure 9:
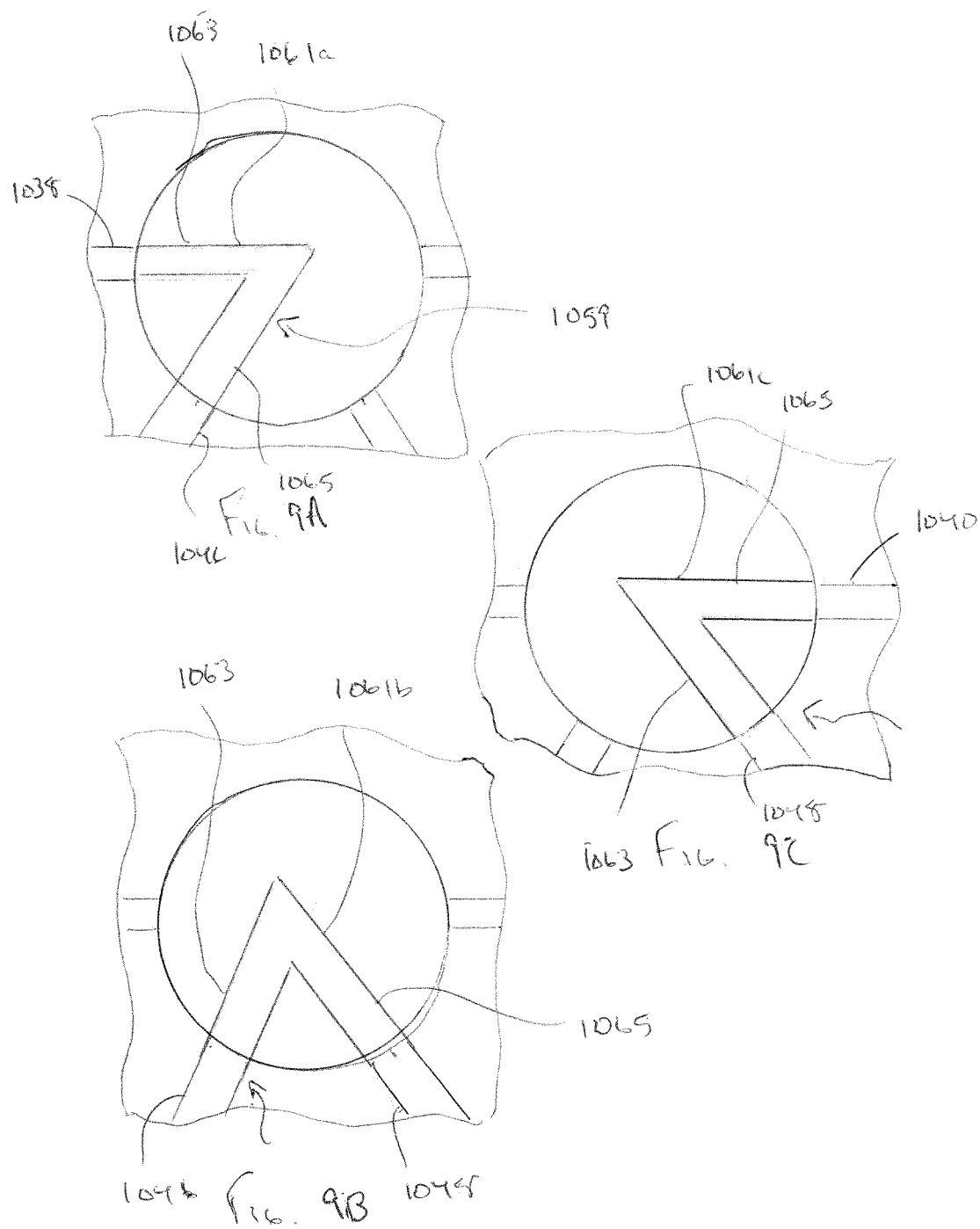
FIGS. 9A, 9B and 9C showing the internal operating components of the stopcock in its various operating modes.

After the gas is transferred from the reservoir first syringe 1080 to the push-draw second syringe 1084, the operator manipulates the valve lever 1067 to rotate the stopcock 1059 to the third position, which is represented by the stopcock channel in position 1061c (and as shown in FIGS. 8 and 9). Therein, the channel segment 1063 is communicably aligned with the passageway 1048 and the channel segment 1065 is similarly aligned with the channel segment 1040. To administer the $CO_2$ in the second syringe 1084 to the patient, the plunger 1083 of the second syringe 1084 is depressed in the direction of arrow 1096. Gas is thereby delivered through the passageway 1048 and the stopcock channel into the passageway 1040. From there, the gas passes in the direction indicated by arrow 1058 through one-way valve 1054 and into tubing 1060. $CO_2$ is thereby transmitted in the direction indicated by arrow 1058 through the one-way valve 1054 and into the tubing 1060 of the outlet section 1014. The one-way valve 1054 prevents backflow of gas into the K-valve control assembly 1016.

The lever 1067 may be configured as an arrow or otherwise marked to include an arrow that points in the direction of the intended fluid flow. With the lever pointing toward the reservoir first syringe 1080, as shown in FIG. 1, the angled channel 1061 is in the position shown in FIGS. 8 and 9A, fluid flow is directed toward the reservoir first syringe 1080. Alternatively, the lever 1067 may be rotated to point toward the second syringe 1084. In this position, the channel is in the position 1061b shown in FIGS. 8 and 9B and $CO_2$ is directed from the first syringe 1080 to the second syringe 1084. Finally, in the third stage of the process, the lever 1067 may be directed to point toward the discharge end of the passageway 1040 and the attached outlet section 1014. In this stage, angled channel 1061 is directed to the position 1061c, shown in FIGS. 8 and 9C, such that fluid flow is directed from second syringe 1084 to the outlet section 1014.

$CO_2$ is delivered through the tube 1060 and into the downstream valve 1064. Once again, a one-way valve 1066 prevents the backflow of gas into the tubing. The stopcock 1070 is operated, as required, to either direct the $CO_2$ to the catheter 1018 and thereby to the patient, or to purge the gas through port 1072. The G-tube seal 1073 prevents air from entering the line.

Accordingly, the flow control system 1010 enables controlled amounts of $CO_2$ to be delivered to the patient in a safe and reliable manner. After the components are connected, they may remain connected during the entire medical procedure and do not then have to be disconnected and reconnected. This minimizes the possibility that air will intrude into the system and endanger the patient. Controlled and precise dosages of $CO_2$ are delivered, by the simple and foolproof operation of the control valve assembly 1016, from the reservoir first syringe 1080 to the push-draw second syringe 1084 and then to the patient. At each stage of the process, the inlet and outlet ends of the valve remain totally isolated from one another so that the risk of administering an explosive and potential deadly dose of $CO_2$ is eliminated.

Figure 10:
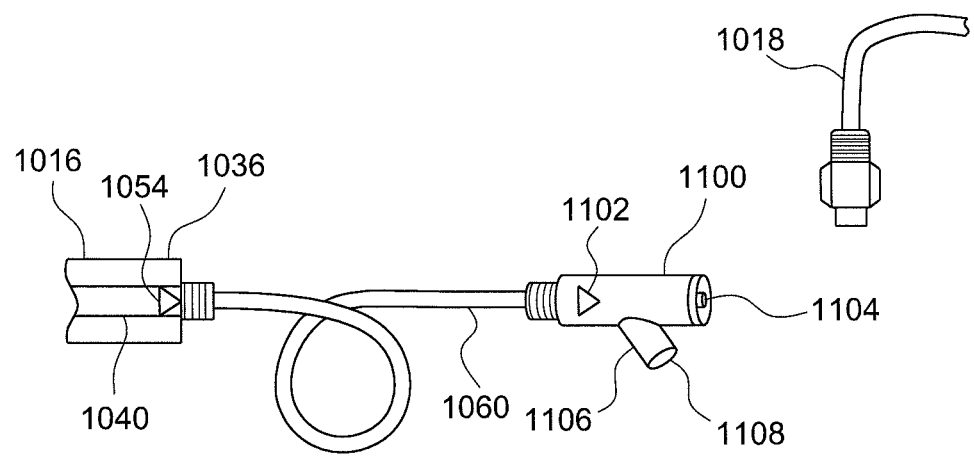
FIG. 10 is a simplified, schematic view of the outlet conduit and an alternative downstream fitting that may be used to interconnect the outlet conduit to the patient catheter.

FIG. 10 again discloses the discharge branch 1036 of the control valve assembly 1016. A one-way valve 1054 is again installed in the passageway 1040 to prevent backflow of gas into the control valve assembly 1016. In this version, the tube 1060 is communicably connected between the discharge branch 1036 and a fitting 1100 that may be used selectively to perform various functions. In particular, the fitting 1100 includes a one-way valve 1102 that prevents backflow of gas into the tube 1060. The fitting 1100 includes a Luer fitting 1104 that allows the fitting 1100 to be releasably attached to the catheter 1018. A flush port 1106 is communicably joined with the fitting 1100 and features a G-valve seal 1108 that permits a syringe (not shown) to be interconnected to the port 1106. This syringe may be used to administer medications through the fitting 1100 to the attached catheter 1018. As a result, such medications may be administered to the patient without having to disconnect the individual components of the fluid delivery system. This saves valuable time in a surgical or medical environment and reduces the risk that air will be introduced into the system. A syringe may also be attached to port 1106 to purge or flush the catheter as needed or desired.

Figure 11:
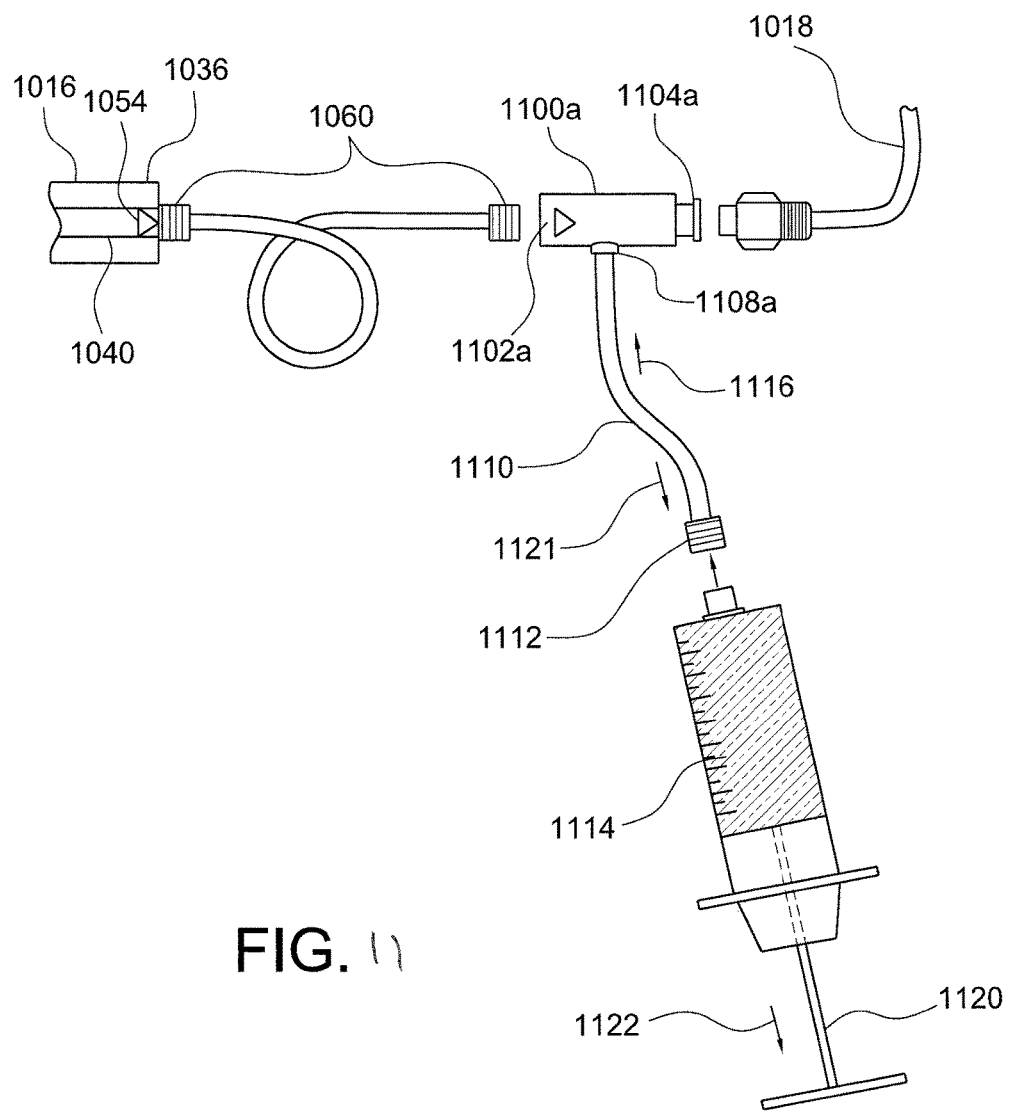
FIG. 11 is a view similar to that of FIGS. 4-6 which depicts a medication administering syringe being attached to the downstream fitting by means of a connecting tube.

FIG. 11 depicts still another embodiment of this invention wherein the medical tube 1060 is communicably interconnected between the discharge branch 1036 of the control valve assembly 1016 and a fitting 1100*a*. The downstream fitting again includes a one-way valve 1102*a* for preventing the backflow of gas or medication into the tube 1060. A Luer fitting 1104*a* releasably interconnects the fitting 1100*a* to the catheter 1018. An inlet/discharge port 1108*a* is formed in the fitting 1100*a* for selectively introducing medication into the patient catheter through the fitting 1100*a* or alternatively purging or flushing the catheter as required. A line 1110 is communicably connected to port 1108*a* and carries at its opposite end a Luer fitting 1112 for releasably attaching the line to a syringe 1114. The syringe 1114 is attached to the line 1100 through the fitting 1112 in order to optionally deliver medication to the catheter 1018 through the fitting 1100*a* in the direction indicated by arrow 1116. Alternatively, fluid may be purged or flushed in the direction of arrow 1121 from the catheter and/or from the system through the line 1110 by drawing the plunger 1120 of the syringe 1114 rearwardly in the directions indicated by arrow 1122.

In alternative versions of this invention, medical fluid may be transmitted from a source to a patient in multiple stages, as described above, but utilizing multiple valves joined to respective syringes. In particular, in a first stage operation, gas or other fluid under pressure is delivered from the source through a first directional valve to a reservoir syringe communicably connected to the first valve. The reservoir syringe is also connected through the first valve to a second valve which is, in turn, communicably joined to a second syringe. The first valve is operated so that the reservoir syringe remains isolated from the second valve as fluid is delivered from the source to the first syringe through the first valve. When a selected volume of fluid is accommodated by the first syringe, the first valve is operated to connect the first syringe with the second valve. The second valve itself is operated to communicably connect the first syringe to the second syringe while, at the same time, isolating the second syringe from the patient. The second syringe is a push-draw syringe. The first syringe is operated with the second valve in the foregoing position to transmit the fluid from the first syringe to the second syringe. During this stage of the operation, both syringes remain isolated from the source and the patient. As a result, even if fluid under pressure is "stacked" in the reservoir syringe, this pressure is not delivered to the patient. Rather, the desired volume of the fluid is delivered instead to the push-draw syringe. The second valve is then operated to communicably join the push-draw syringe to the patient/patient catheter. Once again, the patient and catheter are totally isolated from the source of fluid under pressure. As a result, a safe and selected volume of fluid is delivered from the push-draw syringe to the patient.

Various valve configurations and types of directional valve may be employed to perform the multi-stage delivery described above. In all versions of this invention, it is important that fluid first be delivered from a fluid source to a first syringe and then delivered sequentially to a second syringe. Ultimately, the fluid in the second, push-draw syringe is delivered sequentially to the patient. During each stage of the process, the source of fluid remains isolated from the patient. Typically, only one stage of the system operates at any given time.

Figure 12:
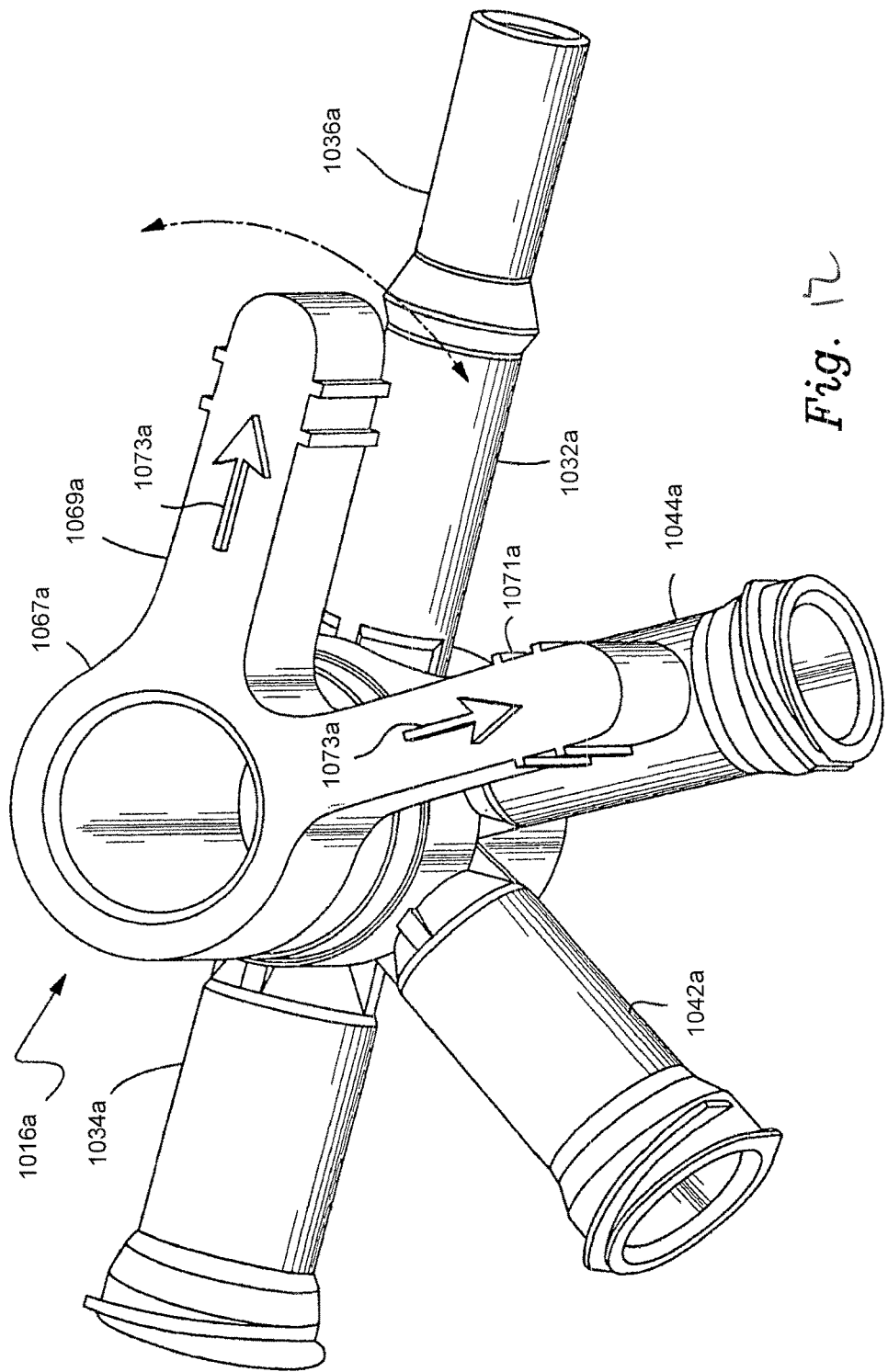
FIG. 12 is a perspective view of a control valve assembly featuring a dual handle for operating the stopcock and indicating which pair of flow passageways is open.

There is shown in FIG. 12 an alternative control valve assembly 1016*a*, which again features a generally K-shaped valve body 1032*a* composed of materials similar to those previously described. Aligned inlet and outlet conduit segments 1034*a*, 1036*a*, as well as transverse or angled conduit segments 1042*a* and 1044*a* are selectively interconnected to communicate and transmit fluid flow through respective pairs of the conduits by a rotatable stopcock valve analogous to that disclosed in the previous embodiment. In this version, the stopcock is rotated by a dual handle valve lever 1067*a*, which includes elongate handles 1069*a*, 1071*a*. These handles 1069*a*, 1071*a* diverge from the hub of the stopcock lever at an angle of approximately 60 degrees, which matches the angle between each adjacent pair of fluid transmitting conduit segments 1034*a*, 1042*a*, 1044*a* and 1036*a* in the control valve assembly 1016*a*. Each of the handles 1069*a*, 1071*a* is elongated and carries a respective directional arrow 1073*a* that is printed, embossed or otherwise formed along the handle.

The valve lever 1067*a* is turned to operate the stopcock such that a selected pair of adjoining conduits is communicably interconnected to permit fluid flow therethrough. In particular, the stopcock is constructed such that the handles 1069*a*, 1071*a* are aligned with and extend along respective conduits that are communicably connected by the stopcock. In other words, the valve lever 1067 is axially rotated until the handles 1069*a*, 1071*a* are aligned with adjoining conduits through which fluid flow is required. The angle between the handles 1069*a*, 1071*a* matches the angle between the adjoining conduits, e.g. 60 degrees. The valve lever 1067*a* may therefore be rotated to align diverging handles 1069*a*, 1071*a* respectively with either conduit segments 1034*a* and 1042*a*, 1042*a* and 1044*a*, or 1044*a* and 1036a. In FIG. 12, the handles 169a, 171a are aligned with conduit segments 1044a and 1036a, and arrows 1073a point in a direction that is substantially aligned with those conduits. This indicates that the valve lever 1067a is rotated and adjusted such that fluid is able to flow through the valve body 1032a from the transverse conduit 1044a to the outlet conduit 1036a. The valve lever 1067a is rotated to selectively align with the other pairs of conduits and thereby open the fluid flow passageway between the selected pair. The use of a dual handle valve lever 1067a clarifies and facilitates usage of the control valve assembly. Otherwise, the valve lever employed in the version of FIG. 12 is constructed and operates analogously to the valve lever disclosed in FIGS. 1, 8 and 9.

The use of multiple syringes is particularly critical and eliminates the risk of stacking that often occurs when a medical fluid is delivered under pressure directly from a source of fluid to a single delivery syringe. In that case, the syringe may be filled with fluid that exceeds the nominal volume of the syringe due to pressure stacking. If such fluid were to be delivered directly to the patient, this could result in a potentially dangerous overdose or fluid flooding. By transmitting the fluid from a reservoir syringe into a second, push-draw syringe, the pressure is equalized and only the fluid volume and pressure accommodated by the second syringe are delivered safely to the patient.

The present system is intended for use in methods and procedures requiring delivery of medical gas. The following are examples of such applications. $CO_2$ is useful in the following arterial procedures: abdominal aortography (aneurysm, stenosis) iliac arteriography (stenosis), runoff analysis of the lower extremities (stenosis, occlusion), renal arteriography (stenosis, arteriovenuous fistula [AVF], aneurysm, tumor), renal arterial transplantation (stenosis, bleeding, AVF), and visceral arteriography (anatomy, bleeding, AVF, tumor). $CO_2$ is useful in the following venous procedures: venography of the upper extremities (stenosis, thrombosis), inferior vena cavography (prior to filter insertion), wedged hepatic venography (visualization of portal vein), direct portography (anatomy, varices), and splenoportograpy (visualization of portal vein). $CO_2$ is likewise useful in the following interventional procedures: balloon angioplasty (arterial venous), stent placement (arterial, venous), embolization (renal, hepatic, pelvic, mesenteric) transjugular intrahepatic portacaval shunt creation, and transcatheter biopsy (hepatic, renal).

Angiography is performed by injecting microbubbles of $CO_2$ through a catheter placed in the hepatic artery following conventional hepatic angiography. Vascular findings on US angiography can be classified into four patterns depending on the tumor vascularity relative to the surrounding liver parenchyma: hypervascular, isovascular, hypovascular, and a vascular spot in a hypovascular background. Improved CT colonography, an accurate screening tool for colorectal cancer, is performed using a small flexible rectal catheter with automated $CO_2$ delivery. This accomplishes improved distention with less post-procedural discomfort.

Carbon dioxide ($CO_2$) gas is used as an alternative contrast to iodinated contrast material. The gas produces negative contrast because of its low atomic number and its low density compared with the surrounding tissues. As such, $CO_2$ doesn't mix with blood so it is not diluted. This property permits excellent central venous visualization from peripheral injections using small needles. Because $CO_2$ doesn't mix with blood, it is not diluted and a peripheral hand injection will yield good opacification centrally. As a result of the fact that $CO_2$ does not mix with blood, when it is injected into a blood vessel, carbon dioxide bubbles displace blood, allowing vascular imaging. Because of the low density of the gas, a digital subtraction angiographic technique is necessary for optimal imaging. The gas bubble can be visible on a standard radiograph and fluoroscopic image.

Because $CO_2$ is present endogenously there is no concern for allergy or renal toxicity, which has been confirmed by numerous animal and human studies. Hawkins I F. *Carbon dioxide digital subtraction arteriography. AJR Am J Roentgenol.* 1982; 139(1):19-24. Hawkins I F, Caridi J G. *Carbon dioxide (CO2) digital subtraction angiography: 26 year experience at the University of Florida. Eur Radiol.* 1998; 8(3):391-402. The viscosity of $CO_2$ is 1/400 that of iodinated contrast and it is also highly soluble, roughly 20 times to 30 times greater than $O_2$. Therefore, it is less occlusive than other gases. When administered intravascularly, it tends to dissolve within a vessel in 30 seconds to 60 seconds. In intravenous administration it is also removed from the lungs in one pass. If $CO_2$ persists in a vessel for more than 30 seconds it is either trapped or there is room air contamination.

As opposed to traditional liquid agents, $CO_2$ does not mix with blood. In fact, $CO_2$ is lighter than blood and floats anterior to it. To render a representative image it must displace the blood in the vessel. As a result, the vessel is less dense and a negative image is obtained with digital subtraction angiography. The quality and accuracy of the image will depend on the amount of blood displaced by the $CO_2$. Typically, smaller vessels, especially those 10 mm or smaller, demonstrate a better correlation with iodinated contrast (FIG. 5). The difficulty sometimes lies in the much larger vessels where a higher volume of $CO_2$ is required. Furthermore, once the total volume of blood has been displaced, using a higher volume of $CO_2$ does not improve the vascular image. Caridi et al. *Carbon Dioxide Digital Subtraction Angiography ($CO_2$ DSA): A Comprehensive User Guide for All Operators. Vascular Disease Management* 2014; 11 (10):E221-E256.

In addition to its buoyancy, when $CO_2$ is administered into the vessel via a catheter it has the potential to fragment into random bubbles depending on how it is delivered. In an attempt to avoid this, the catheter should be purged prior to definitive delivery and a continuous, controlled delivery of the volume of choice should be given. Dr. Cho studied the best catheter to administer a uniform, organized bolus of gas to minimalize the bubbling effect. He found that an end-hole catheter yielded the best results.

It is also appreciated that $CO_2$ can easily be administered in significant doses and has the advantage of central reflux resulting in opacification of the entire vascular structure (FIG. 12). As opposed to $CO_2$, contrast will only demonstrate distal to the catheter. This is especially useful in procedures such as renal stent deployment in which intervention is central to the catheter tip. The position of the stenosis and ostium can always be visualized using $CO_2$ reflux.

$CO_2$ insufflation for colonoscopy improves productivity of the endoscopy unit. Endoscopic thyroid resection involves creating a working space within the neck using $CO_2$ insufflation devices, with both axillary and neck approaches as starting points for dissection. $CO_2$ insufflators are used during laparoscopic surgery.

Because of the lack of nephrotoxicity and allergic reactions, $CO_2$ is increasingly used as a contrast agent for diagnostic angiography and vascular interventions in both the arterial and venous circulation. $CO_2$ is particularly useful in patients with renal insufficiency or a history of hypersensitivity to iodinated contrast medium.

$CO_2$ is compressible during injection and extends in the vessel as it exits the catheter. $CO_2$ is lighter than blood plasma; therefore, it floats above the blood. When injected into a large vessel such as the aorta or inferior vena cava, $CO_2$ bubbles flow along the anterior part of the vessel with incomplete blood displacement along the posterior portion. $CO_2$ causes no allergic reaction. Because $CO_2$ is a natural byproduct, it has no likelihood of causing a hypersensitivity reaction. Therefore, the gas is an ideal alternative. Unlimited amounts of $CO_2$ can be used for vascular imaging because the gas is effectively eliminated by means of respiration. $CO_2$ is partially useful in patients with compromised cardiac and renal function who are undergoing complex vascular interventions.

Intranasal carbon dioxide is very promising as a safe and effective treatment to provide rapid relief for seasonal allergic rhinitis. $CO_2$ is used for transient respiratory stimulation; encouragement of deep breathing and coughing to prevent or treat aterectasis; to provide a close-to-physiological atmosphere (mixed with oxygen) for the operation of artificial organs such as the membrane dialyzer (kidney) and the pump oxygenator; and for injection into body cavities during surgical procedures.

Medical asepsis is accomplished by using $CO_2$ with an implant device prior to surgical implantation. $CO_2$ may be effectively delivered to a foam generating tip for creating a medical foam for use in wound care and hair loss treatment.

Additionally, the present invention is used in methods requiring the delivery of other gasses such as: Carbon Dioxide U.S.P., Medical Air U.S.P., Helium U.S.P., Nitrogen U.S.P., Nitrous Oxide U.S.P., Oxygen U.S.P. and any combination thereof.

From the foregoing it may be seen that the apparatus of this invention provides for a system for safely delivering a controlled volume of a medical fluid in the form of a gas to a patient and, more particularly to a system for delivery a controlled flow of carbon dioxide ($CO_2$) or other contrast media in order to obtain radiological images. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

While the invention has been described in its preferred form or embodiment with some degree of particularity, it is understood that this description has been given only by way of example, and that numerous changes in the details of construction, fabrication, and use, including the combination and arrangement of parts, may be made without departing from the spirit and scope of the invention.

The invention claimed is:

1. A method for performing a medical procedure requiring effective and reliable delivery of controlled amounts of a medical grade gas to a patient, comprising:
    providing a compressed gas cylinder having a weight with medical grade gas sealed therein of at least twelve grams and not greater than fifty grams, the compressed gas cylinder including an elongate, generally cylindrical body having an interior chamber accommodating a compressed and sterile medical grade gas therein, wherein said cylindrical body is of a triple washed construction for holding the medical grade gas within said interior chamber of said cylindrical body under pressure;
    connecting the compressed gas cylinder to an integrated compressed gas unit including an inlet port to which the compressed gas cylinder is selectively connected and an outlet port in communication with the inlet port, the integrated compressed gas unit also including a regulator valve assembly positioned between the outlet port and the inlet port, wherein the regulator valve assembly includes a regulator adjustment dial;
    securing a flow control system to the compressed gas unit;
    delivering the medical grade gas in controlled amounts by actuating the compressed gas unit and operating the flow control system to deliver the medical grade gas.

2. A method for performing a medical procedure according to claim 1, wherein an end portion of compressed gas cylinder is encircled by a thread for attaching said cartridge to a medical apparatus requiring compressed gas of the type contained by said cartridge.

3. A method for performing a medical procedure according to claim 2, wherein said thread is at least ¼" (6.35 mm) and not greater than 1" (25.4 mm).

4. A method for performing a medical procedure according to claim 1, wherein the medical grade gas is $CO_2$.

5. A method for performing a medical procedure according to claim 4, wherein the step of delivering includes delivering $CO_2$ for the purpose of imaging.

6. A method for performing a medical procedure according to claim 4, wherein the step of delivering includes delivering $CO_2$ for the purpose of medical diagnosis and therapy.

7. A method for performing a medical procedure according to claim 4, wherein the step of delivering includes delivering $CO_2$ for the purpose of apply $CO_2$ as an alternative to iodinated contrast.

8. A method for performing a medical procedure according to claim 4, wherein the step of delivering includes delivering CO, for the purpose of acting as a medical device for minimal access vascular procedures.

9. A method for performing a medical procedure according to claim 4, wherein the step of delivering includes delivering $CO_2$ for the purpose of in vivo diagnostic use for carrying solutions to stabilize micro bubbles for ultrasound, radiographic or fluoroscopic imaging.

\* \* \* \* \*